(12) United States Patent
Elahi et al.

(10) Patent No.: US 8,644,918 B2
(45) Date of Patent: *Feb. 4, 2014

(54) METHOD AND APPARATUS FOR RATE ACCURACY ENHANCEMENT IN VENTRICULAR TACHYCARDIA DETECTION

(75) Inventors: Bijan Elahi, Bellevue, WA (US); Joseph M. Bocek, Seattle, WA (US); Jaeho Kim, Redmond, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/871,337

(22) Filed: Aug. 30, 2010

(65) Prior Publication Data

US 2010/0324613 A1 Dec. 23, 2010

Related U.S. Application Data

(60) Continuation of application No. 12/069,451, filed on Feb. 8, 2008, now Pat. No. 7,797,037, which is a division of application No. 11/054,726, filed on Feb. 10, 2005, now Pat. No. 7,346,388.

(51) Int. Cl.
*A61B 5/0464* (2006.01)

(52) U.S. Cl.
USPC ....................................... 600/518

(58) Field of Classification Search
USPC ................. 600/509, 515, 516, 518, 519
See application file for complete search history.

(56) References Cited

U.S. PATENT DOCUMENTS

| | | | |
|---|---|---|---|
| 5,628,326 A | | 5/1997 | Arand et al. |
| 5,730,141 A | * | 3/1998 | Fain et al. ............... 600/518 |
| 5,941,831 A | | 8/1999 | Turcott |
| 5,978,707 A | | 11/1999 | Krig et al. |
| 6,493,579 B1 | | 12/2002 | Gilkerson et al. |
| 6,522,925 B1 | | 2/2003 | Gilkerson et al. |
| 6,611,713 B2 | | 8/2003 | Schauerte |
| 7,346,388 B2 | | 3/2008 | Elahi et al. |
| 2006/0178704 A1 | | 8/2006 | Elahi et al. |
| 2008/0147132 A1 | | 6/2008 | Elahi et al. |

OTHER PUBLICATIONS

"U.S. Appl. No. 12/069,451 Non Final Office Action Mailed Oct. 1, 2009", 10 pgs.
"U.S. Appl. No. 11/054,726 , Final Office Action mailed May 24, 2007", 6 pgs.
"U.S. Appl. No. 11/054,726 , Non-Final Office Action mailed Jan. 22, 2007", 9 pgs.
"U.S. Appl. No. 11/054,726, Advisory Action mailed Aug. 6, 2007", 3 pgs.
"U.S. Appl. No. 11/054,726, Notice of Allowance mailed Oct. 22, 2007", 4 pgs.
"U.S. Appl. No. 11/054,726, Response filed Apr. 23, 2007 to Non-Final Office Action mailed Jan. 22, 2007", 14 pgs.

(Continued)

*Primary Examiner* — Allen Porter, Jr.
(74) *Attorney, Agent, or Firm* — Schwegman Lundberg & Woessner, P.A.

(57) ABSTRACT

An implantable cardioverter/defibrillator (ICD) executes a rate accuracy enhancement algorithm to select measured atrial and ventricular intervals for classifying a detected tachycardia based on average atrial and ventricular rates calculated from the selected atrial and ventricular intervals. The detected tachycardia is classified as ventricular tachycardia (VT) if the average ventricular rate is substantially higher than the average atrial rate.

20 Claims, 10 Drawing Sheets

(56) References Cited

OTHER PUBLICATIONS

"U.S. Appl. No. 11/054,726, Response filed Jul. 24, 2007 to Final Office Action mailed May 24, 2007", 14 pgs.

"U.S. Appl. No. 12/069,451, Notice of Allowance mailed May 12, 2010", 4 Pages.

"U.S. Appl. No. 12/069,451, Response filed Feb. 1, 2010 to Non Final Office Action mailed Oct. 1, 2009", 15 pgs.

* cited by examiner

METHOD AND APPARATUS FOR RATE ACCURACY ENHANCEMENT IN VENTRICULAR TACHYCARDIA DETECTION

CLAIM OF PRIORITY

This application is a continuation of and claims the benefit of priority under 35 U.S.C. §120 to U.S. patent application Ser. No. 12/069,451, filed on Feb. 8, 2008, now U.S. Pat. No. 7,797,037 which is a divisional of and claims the benefit of priority under 35 U.S.C. §120 to U.S. application Ser. No. 11/054,726, filed Feb. 10, 2005, now U.S. Pat. No. 7,346,388, the specifications of which are herein incorporated by reference.

TECHNICAL FIELD

This document relates generally to cardiac rhythm management (CRM) systems and particularly, but not by way of limitation, to an implantable cardioverter/defibrillator (ICD) including an enhanced tachycardia detection system that detects and classifies ventricular tachycardia (VT) based on analysis of atrial and ventricular rates.

BACKGROUND

The heart is the center of a person's circulatory system. The left portions of the heart, including the left atrium (LA) and left ventricle (LV), draw oxygenated blood from the lungs and pump it to the organs of the body to provide the organs with their metabolic needs for oxygen. The right portions of the heart, including the right atrium (RA) and right ventricle (RV), draw deoxygenated blood from the body organs and pump it to the lungs where the blood gets oxygenated. These mechanical pumping functions are accomplished by contractions of the heart. In a normal heart, the sinoatrial (SA) node, the heart's natural pacemaker, generates electrical impulses, called action potentials, that propagate through an electrical conduction system to various regions of the heart to cause the muscular tissues of these regions to depolarize and contract. The electrical conduction system includes, in the order by which the electrical impulses travel in a normal heart, internodal pathways between the SA node and the atrioventricular (AV) node, the AV node, the His bundle, and the Purkinje system including the right bundle branch (RBB, which conducts the electrical impulses to the RV) and the left bundle branch (LBB, which conducts the electrical impulses to the LV). More generally, the electrical impulses travel through an AV conduction pathway to cause the atria, and then the ventricles, to contract.

Tachycardia (also referred to as tachyarrhythmia) occurs when the heart contracts at a rate higher than a normal heart rate. Tachycardia generally includes ventricular tachycardia (VT) and supraventricular tachycardia (SVT). VT occurs, for example, when a pathological conduction loop formed in the ventricles through which electrical impulses travel circularly within the ventricles, or when a pathologically formed electrical focus generates electrical impulses from the ventricles. SVT includes physiologic sinus tachycardia and pathologic SVTs. The physiologic sinus tachycardia occurs when the SA node generates the electrical impulses at a particularly high rate. A pathologic SVT occurs, for example, when a pathologic conduction loop forms in an atrium. Fibrillation occurs when the heart contracts at a tachycardia rate with an irregular rhythm. Ventricular fibrillation (VF), as a ventricular arrhythmia with an irregular conduction, is a life threatening condition requiring immediate medical treatment such as ventricular defibrillation. Atrial fibrillation (AF), as an SVT with an irregular rhythm, though not immediately life threatening, also needs medical treatment such as atrial defibrillation to restore a normal cardiac function and prevents the deterioration of the heart.

Implantable cardioverter/defibrillators (ICDs) are used to treat tachycardias, including fibrillation. To deliver an effective cardioversion/defibrillation therapy, the cardioversion/defibrillation energy is to be delivered to the chambers of the heart where the tachycardia or fibrillation originates. A cardioversion/defibrillation pulse delivered to a wrong chamber may be ineffective in treating the tachycardia or fibrillation and may cause unnecessary discomfort to the patient and shorten the ICD's battery life. When the atrial rate of depolarizations (or contractions) is substantially different from the ventricular rate of depolarizations (or contractions), the atrial and ventricular rates provide for a basis for locating where the tachycardia originates. However, events such as premature contractions, undersensing, and oversensing affect measured atrial and ventricular rates but are unrelated to the origin of tachycardia. Therefore, there is a need for improving accuracy in locating the origin of tachycardia based on measured atrial and ventricular rates.

SUMMARY

An ICD executes a rate accuracy enhancement algorithm to select measured atrial and ventricular intervals for classifying a detected tachycardia based on average atrial and ventricular rates calculated from the selected atrial and ventricular intervals. The detected tachycardia is classified as VT if the average ventricular rate is substantially higher than the average atrial rate.

In one embodiment, an ICD includes a sensing circuit, an interval measurement circuit, a tachycardia detection circuit, and a detection enhancement circuit. The sensing circuit senses an atrial electrogram and a ventricular electrogram. The interval measurement circuit measures atrial intervals from the atrial electrogram and ventricular intervals from the ventricular electrogram. The tachycardia detection circuit detects a tachycardia based on at least one of the measured atrial intervals and the measured ventricular intervals. The detection enhancement circuit includes a rate accuracy enhancement module, a rate calculator, and a tachycardia classification module. The rate accuracy enhancement module executes a rate accuracy enhancement algorithm to select a plurality of atrial intervals from the measured atrial intervals and a plurality of ventricular intervals from the measured ventricular intervals. The rate calculator calculates at least one average atrial rate based on the selected plurality of atrial intervals and at least one average ventricular rate based on the selected plurality of ventricular intervals. The tachycardia classification module classifies the detected tachycardia as VT when the average ventricular rate is substantially higher than the average atrial rate.

In one embodiment, a method for enhancing tachycardia detection is provided. An atrial electrogram and a ventricular electrogram are sensed. Atrial intervals are measured based on the sensed atrial electrograms, and ventricular intervals are measured based on the sensed ventricular electrograms. A tachycardia is being detected based on one or more of the measured ventricular intervals. A rate accuracy enhancement algorithm is executed to select at least a plurality of atrial intervals from the measured atrial intervals and a plurality of ventricular intervals from the measured ventricular intervals. At least one average atrial rate is calculated based on the selected plurality of atrial intervals and one average ventricular rate is calculated based on the selected plurality of ventricular intervals. The detected tachycardia is classified VT if the at least one average ventricular rate is higher than the at least one average atrial rate by a predetermined margin.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

The drawings, which are not necessarily drawn to scale, illustrate generally, by way of example, but not by way of limitation, various embodiments discussed in the present document.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

This document discusses, among other things, a CRM system including an ICD having an enhanced tachycardia detection system. The enhanced tachycardia detection system measures atrial and ventricular intervals (or rates) from atrial and ventricular electrograms. Tachycardia is detected based on one of the atrial and ventricular intervals (or rates). The detected tachycardia is classified as VT if an average ventricular rate is substantially higher than an average atrial rate during the tachycardia. The average atrial and ventricular rates are calculated from selected measured atrial and ventricular intervals. To select the measured atrial and ventricular intervals, a rate accuracy enhancement algorithm is executed to improve the accuracy of the classification by reducing the effect of factors unrelated to tachycardia, such as undersensing, oversensing, and premature contractions. The ICD delivers a ventricular cardioversion/defibrillation pulse in response to a VT classification.

Figure 1:
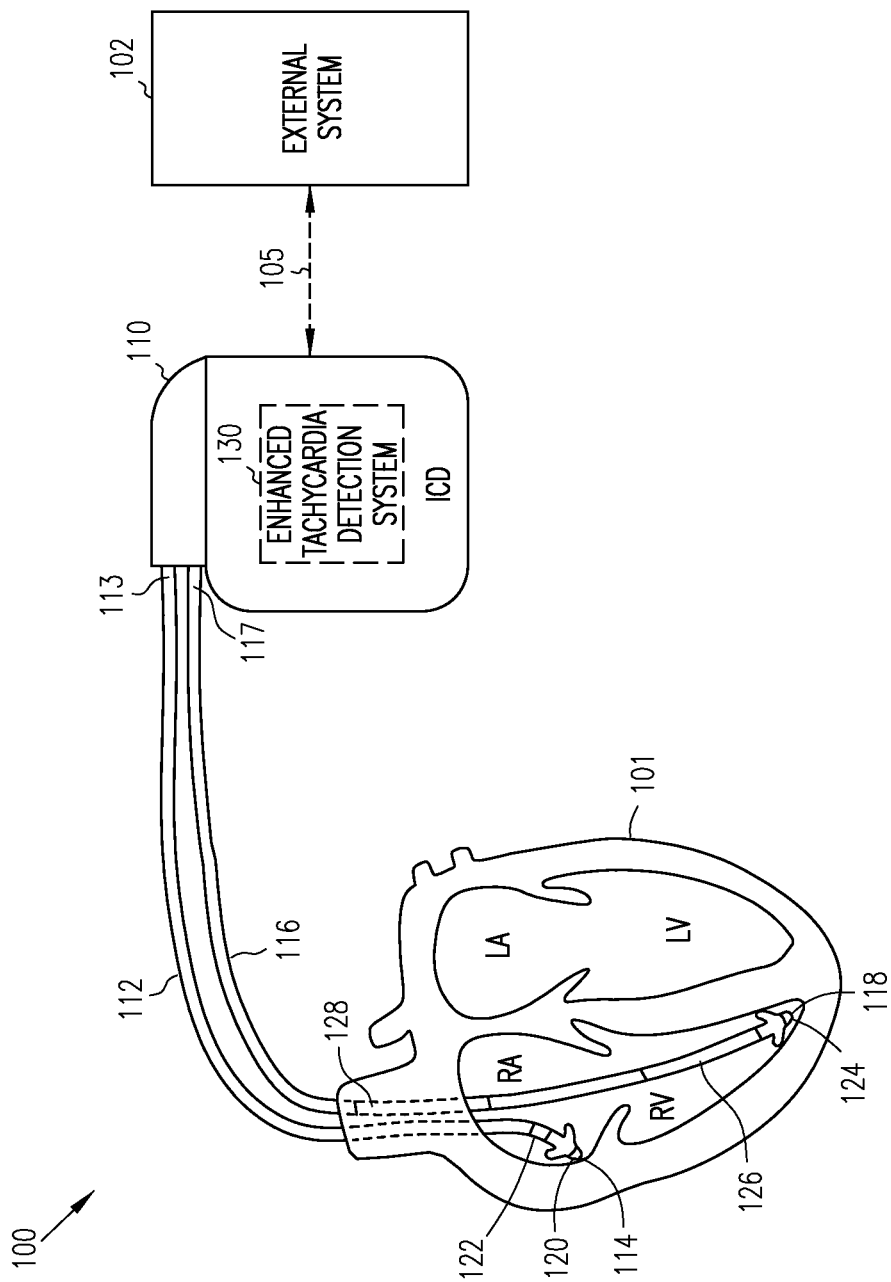
FIG. 1 is an illustration of one embodiment of a CRM system including an ICD and portions of the environment in which the CRM system operates.

FIG. 1 is an illustration of one embodiment of a CRM system 100 and portions of the environment in which CRM system 100 operates. CRM system 100 includes an ICD 110 that is electrically coupled to a heart 101 through leads 112 and 116. An external system 102 communicates with ICD 110 via a telemetry link 105.

ICD 110 includes a hermetically sealed can housing an electronic circuit that senses physiological signals and delivers therapeutic electrical pulses. The hermetically sealed can also functions as an electrode for sensing and/or pulse delivery purposes. In one embodiment, as illustrated in FIG. 1, the electronic circuit senses at least an atrial electrogram and a ventricular electrogram from heart 101 and delivers pacing and cardioversion/defibrillation pulses to heart 101. Lead 112 is a pacing lead that includes a proximal end 113 connected to ICD 110 and a distal end 114 disposed in the right atrium (RA) of heart 101. A pacing-sensing electrode 120 is located at distal end 114. Another pacing-sensing electrode 122 is located near distal end 114. Electrodes 120 and 122 are electronically connected to ICD 110 to allow sensing of the atrial electrogram and/or delivery of atrial pacing pulses. Lead 116 is a pacing/defibrillation lead that includes a proximal end 117 connected to ICD 110 and a distal end 118 disposed in the right ventricle (RV) of heart 101. A pacing-sensing electrode 124 is located at distal end 118. A defibrillation electrode 126 is located near distal end 118 but electrically separated from pacing-sensing electrode 124. Another defibrillation electrode 128 is located at a distance from distal end 118 for supraventricular placement. Electrodes 124, 126, and 128 are electrically connected to ICD 110. Electrode 124 allows sensing of the ventricular electrogram and/or delivery of ventricular pacing pulses. Electrode 126 allows delivery of cardioversion/defibrillation pulses to a ventricular region and, in one embodiment, serves as a return electrode for delivery of ventricular pacing pulses. Electrode 128 serves as a return electrode for the cardioversion/defibrillation pulses delivered through electrode 126.

ICD 110 includes an enhanced tachycardia detection system 130. A cardioversion/defibrillation pulse is delivered to the ventricular region after enhanced tachycardia detection system 130 detects a tachycardia and classifies the detected tachycardia as a VT. Enhanced tachycardia detection system 130 detects the tachycardia based on one of the atrial and ventricular electrograms. The detected tachycardia is classified as VT if the ventricles contract at a substantially higher rate than the atria during the tachycardia. Enhanced tachycardia detection system 130 executes a rate accuracy enhancement algorithm to select measured intervals between consecutive atrial contractions and between consecutive ventricular contractions for determining whether the ventricles depolarize at a higher rate than the atria. The rate accuracy enhancement algorithm is designed to reduce the effect of factors that may lead to misclassification of the detected tachycardia, such as undersensing, oversensing, and premature contractions.

External system 102 allows for programming of ICD 110 and receives signals acquired by ICD 110. In one embodiment, external system 102 includes a programmer. In another embodiment, external system 102 is a patient management system including an external device in proximity of ICD 110, a remote device in a relatively distant location, and a telecommunication network linking the external device and the remote device. The patient management system allows access to ICD 110 from a remote location, for purposes such as monitoring patient status and adjusting therapies. In one embodiment, telemetry link 105 is an inductive telemetry link. In an alternative embodiment, telemetry link 105 is a far-field radio-frequency telemetry link. Telemetry link 105 provides for data transmission from ICD 110 to external system 102. This may include, for example, transmitting real-time physiological data acquired by ICD 110, extracting physiological data acquired by and stored in ICD 110, extracting therapy history data stored in ICD 110, and extracting data indicating an operational status of ICD 100 (e.g., battery status and lead impedance). Telemetry link 105 also provides for data transmission from external system 102 to ICD 110. This may include, for example, programming ICD 110 to acquire physiological data, programming ICD 110 to perform at least one self-diagnostic test (such as for a device operational status), programming ICD 110 to run a signal analysis algorithm (such as an algorithm implementing the tachycardia detection and classification methods discussed in this document), and programming ICD 110 to deliver pacing and/or cardioversion/defibrillation therapies.

Figure 2:
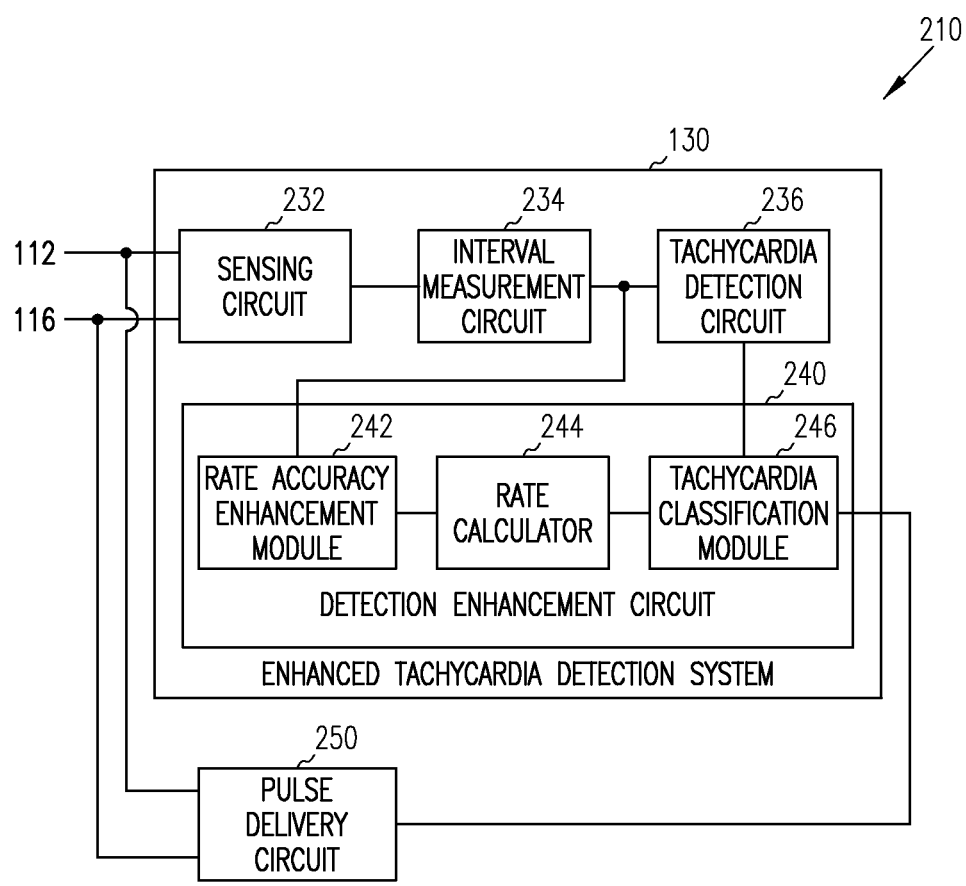
FIG. 2 is a block diagram illustrating an embodiment of portions of the circuit of the ICD.

FIG. 2 is a block diagram illustrating an embodiment of a circuit 210 including potions of the circuit of ICD 110. Circuit 210 includes enhanced tachycardia detection system 130 and a pulse delivery circuit 250.

Enhanced tachycardia detection system 130 includes a sensing circuit 232, an interval measurement circuit 234, a tachycardia detection circuit 236, and a detection enhancement circuit 240. Sensing circuit 232 senses the atrial electrogram and the ventricular electrogram. Interval measurement circuit 234 measures atrial intervals from the atrial electrogram and ventricular intervals from the ventricular electrogram. An atrial interval is a time interval between two adjacent atrial depolarizations (P waves). A ventricular interval is a time interval between two adjacent ventricular depolarizations (R waves). Tachycardia detection circuit 236 detects tachycardia based on at least one of the atrial intervals and the ventricular intervals. In one embodiment, tachycardia detection circuit 236 detects a tachycardia when the ventricular interval falls below a tachycardia threshold interval. Detection enhancement circuit 240 classifies the detected tachycardia as VT based on a further analysis of the atrial and ventricular intervals. In one embodiment, detection enhancement circuit 240 includes portions of a processor circuit, such as a microprocessor, a microcontroller, or a custom integrated circuit, that are programmed to perform the detection enhancement functions discussed in this document.

Detection enhancement circuit 240 includes a rate accuracy enhancement module 242, a rate calculator 244, and a tachycardia classification module 246. According to a rate accuracy enhancement algorithm, to enhance the accuracy of rate calculation performed by rate calculator 244, rate accuracy enhancement module 242 selects a plurality of atrial intervals from the measured atrial intervals and a plurality of ventricular intervals from the measured ventricular intervals. Rate calculator 244 calculates at least one average atrial rate based on the selected plurality of atrial intervals and at least one average ventricular rate based on the selected plurality of ventricular intervals. The atrial rate is the number of the intervals in the plurality of atrial intervals divided by the sum of the intervals in the plurality of atrial intervals, expressed as beats per minute. The ventricular rate is the number of the intervals in the plurality of ventricular intervals divided by the sum of the intervals in the plurality of ventricular intervals, expressed as beats per minute.

Tachycardia classification module 246 classifies the detected tachycardia as VT when the average ventricular rate is substantially higher than the average atrial rate. In one embodiment, tachycardia classification module 246 classifies the detected tachycardia as VT when the average ventricular rate is higher than the average atrial rate by a predetermined margin. In one specific embodiment, the margin is about 10 beats per minute. In another specific embodiment, tachycardia classification module 246 includes a margin controller to program the margin. In a further embodiment, if the average ventricular rate is substantially lower than the average atrial rate, tachycardia classification module 246 classifies the tachycardia as SVT or dual arrhythmia. A further analysis is performed to distinguish between SVT and dual arrhythmia. If the average ventricular rate is substantially equal to the average atrial rate, tachycardia classification module 246 classifies the tachycardia as a 1:1 tachycardia, i.e., a tachycardia with one-to-one association between atrial and ventricular depolarizations. In one specific embodiment, tachycardia classification module 246 performs a morphological analysis on the correlation between an arrhythmic waveform and a template waveform recorded during a known rhythm to further classify the 1:1 tachycardia as one of VT and SVT. The arrhythmic waveform is a segment of an electrogram representing a heart beat sensed during the 1:1 tachycardia.

Pulse delivery circuit 250 includes a cardioversion/defibrillation circuit that delivers cardioversion/defibrillation pulses. In one embodiment, pulse delivery circuit 250 also includes a pacing circuit to deliver pacing pulses. The cardioversion/defibrillation circuit delivers a ventricular pulse through lead 116 and electrode 126 if the detected tachycardia is classified as VT.

Figure 3:
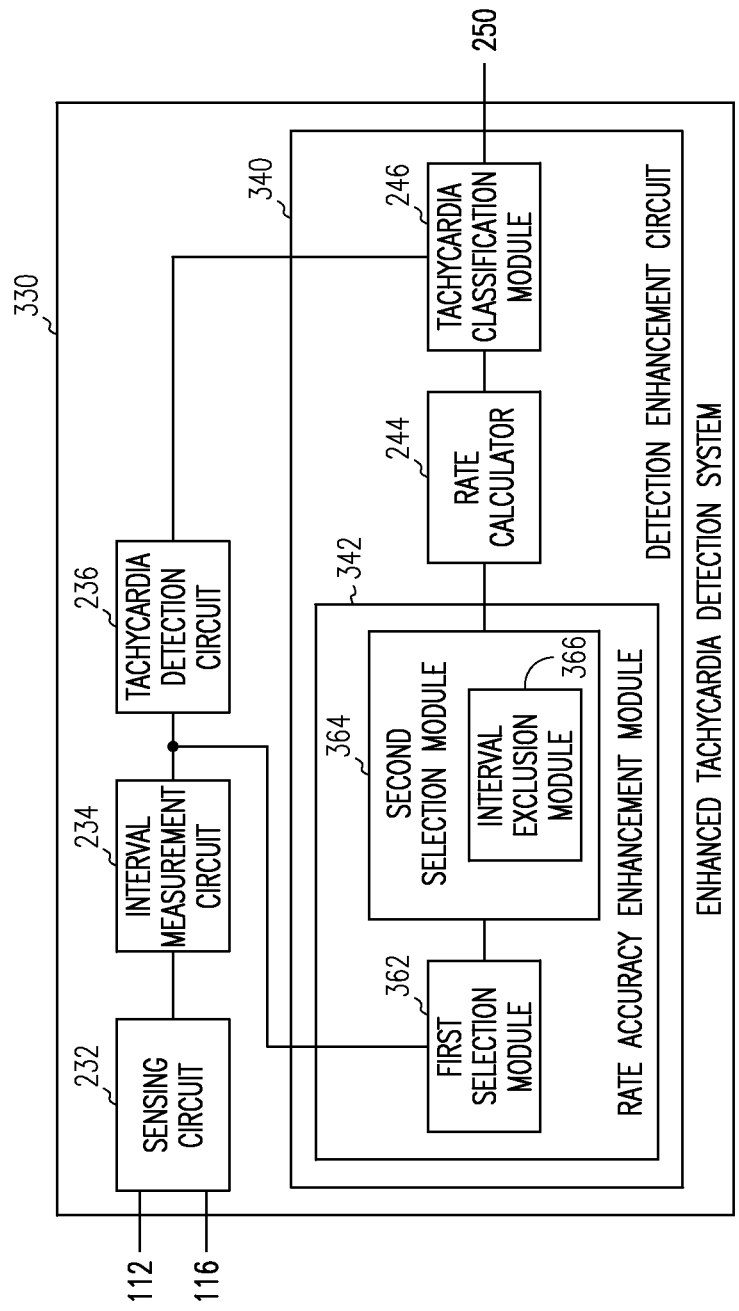
FIG. 3 is a block diagram illustrating an embodiment of the circuit of an enhanced tachycardia detection system.

FIG. 3 is a block diagram illustrating an embodiment of the circuit of an enhanced tachycardia detection system 330, which is one specific embodiment of enhanced tachycardia detection system 130. Enhanced tachycardia detection system 330 includes sensing circuit 232, interval measurement circuit 234, tachycardia detection circuit 236, and a detection enhancement circuit 340. Detection enhancement circuit 340 is a specific embodiment of detection enhancement circuit 240 and includes a rate accuracy enhancement module 342, rate calculator 244, and tachycardia classification module 246. Rate accuracy enhancement module 342 is a specific embodiment of rate accuracy enhancement module 242.

To enhance the accuracy of rate calculation performed by rate calculator 244, rate accuracy enhancement module 342 executes a rate accuracy enhancement algorithm designed to exclude certain outlier (shortest and longest) intervals from being used in the calculation of the average atrial and ventricular rates. Rate accuracy enhancement module 342 includes a first selection module 362 and a second selection module 364. First selection module 362 selects a set of atrial intervals from the measured atrial intervals and a set of ventricular intervals from the measured ventricular intervals. In one embodiment, the set of atrial intervals includes a predetermined number of atrial intervals, and the set of ventricular intervals includes a predetermined number of ventricular intervals. In another embodiment, first selection module 362 includes a set size module to determine a size of the set of atrial intervals and a size of the set of ventricular intervals based on one or more measured atrial intervals and/or one or more measured ventricular intervals. In one specific embodiment, the size of the set of atrial intervals and the size of the set of ventricular intervals are equal.

Second selection module 364 selects a subset of atrial intervals from the selected set of atrial intervals and a subset of ventricular intervals from the selected set of ventricular intervals. In one embodiment, as illustrated in FIG. 3, second selection module 364 includes an interval exclusion module 366. Interval exclusion module 366 excludes one or more intervals from each of the set of atrial intervals and the set of ventricular intervals. According predetermined exclusion criteria, interval exclusion module 366 excludes one or more shortest intervals and one or more longest intervals from the set of atrial intervals and the set of ventricular intervals. In one embodiment, a predetermined number of intervals are excluded from each of the set of atrial intervals and the set of ventricular intervals. In another embodiment, interval exclusion module 366 includes an exclusion size module to determine the number of intervals to be excluded from each of the set of atrial intervals and the set of ventricular intervals based on the atrial and ventricular rates. Interval exclusion module 366 comprises an outlier interval detector to detect the intervals to be excluded. In one specific embodiment, according to the predetermined exclusion criteria, the outlier detector detects one or more shortest atrial intervals and one or more longest atrial intervals from the set of atrial intervals and detects one or more shortest ventricular intervals and one or more longest ventricular intervals from the set of ventricular intervals. In another specific embodiment, according to the predetermined exclusion criteria, the outlier detector detects one or more longest atrial intervals from the set of atrial intervals and one or more shortest ventricular intervals from the set of ventricular intervals.

Rate calculator 244 calculates the average atrial rate based on the selected subset of atrial intervals and the average ventricular rate based on the selected subset of ventricular intervals. In one embodiment, the subset of atrial intervals includes about 10 atrial intervals, and the subset of ventricular intervals includes about 10 ventricular intervals.

Figure 4:
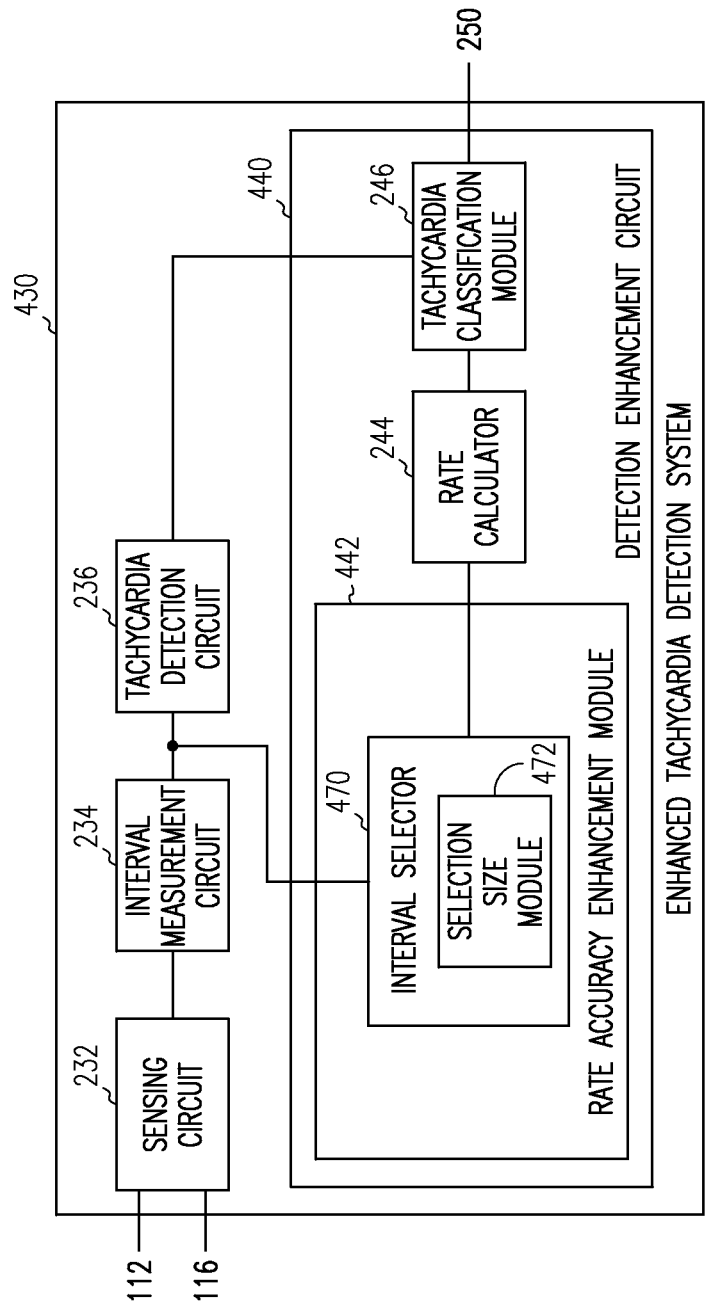
FIG. 4 is a block diagram illustrating an embodiment of the circuit of another enhanced tachycardia detection system.

FIG. 4 is a block diagram illustrating an embodiment of the circuit of another enhanced tachycardia detection system 430, which is another specific embodiment of enhanced tachycardia detection system 130. Enhanced tachycardia detection system 430 includes sensing circuit 232, interval measurement circuit 234, tachycardia detection circuit 236, and a detection enhancement circuit 440. Detection enhancement circuit 440 is another specific embodiment of detection enhancement circuit 240 and includes a rate accuracy enhancement module 442, rate calculator 244, and tachycardia classification module 246. Rate accuracy enhancement module 442 is another specific embodiment of rate accuracy enhancement module 242.

To enhance the accuracy of rate calculation performed by rate calculator 244, rate accuracy enhancement module 442 executes a rate accuracy enhancement algorithm designed to determine the number of intervals used to calculate each average rate based on the heart rate as indicated by one or more measured atrial or ventricular intervals. Rate accuracy enhancement module 442 includes an interval selector 470 that selects a set of atrial intervals from the measured atrial intervals and a set of ventricular intervals from the measured ventricular intervals. Interval selector 470 includes a selection size module 472 that determines a size of the set of atrial intervals and a size of the set of ventricular intervals based on one or more measured atrial intervals and/or one or more measured ventricular intervals. In one specific embodiment, the size of the set of atrial intervals and the size of the set of ventricular intervals are equal. In one specific embodiment, the size of the set of atrial intervals and the size of the set of ventricular intervals are both set to about 10.

Rate calculator 244 calculates the average atrial rate based on the selected set of atrial intervals and the average ventricular rate based on the selected set of ventricular intervals.

Figure 5:
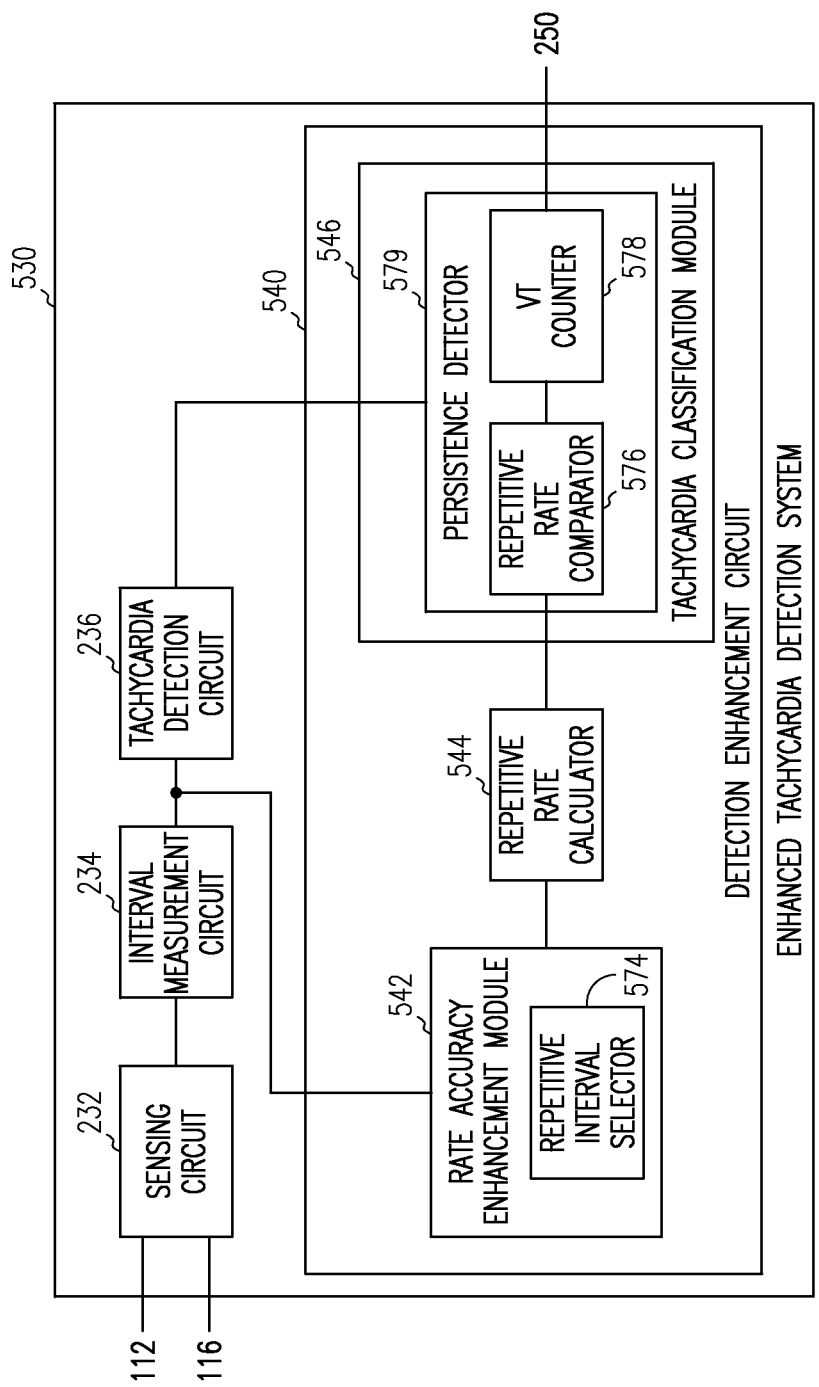
FIG. 5 is a block diagram illustrating an embodiment of the circuit of another enhanced tachycardia detection system.

FIG. 5 is a block diagram illustrating an embodiment of the circuit of another enhanced tachycardia detection system 530, which is another specific embodiment of enhanced tachycardia detection system 130. Enhanced tachycardia detection system 530 includes sensing circuit 232, interval measurement circuit 234, tachycardia detection circuit 236, and a detection enhancement circuit 540. Detection enhancement circuit 540 is another specific embodiment of detection enhancement circuit 240 and includes a rate accuracy enhancement module 542, a repetitive rate calculator 544, and a tachycardia classification module 546. Rate accuracy enhancement module 542 is another specific embodiment of rate accuracy enhancement module 242. Repetitive rate calculator 544 is a specific embodiment of rate calculator 244. Tachycardia classification module 546 is a specific embodiment of tachycardia classification module 246.

To enhance the accuracy of rate calculation performed by repetitive rate calculator 544, rate accuracy enhancement module 542 executes a rate accuracy enhancement algorithm designed to classify the detected tachycardia as VT based on persistent tachycardia detection with VT classification. Rate accuracy enhancement module 542 includes a repetitive interval selector 574 that selects a set of atrial intervals from the measured atrial intervals and a corresponding set of ventricular intervals from the measured ventricular intervals for each heart beat for a plurality of heart beats detected during an episode of the detected tachycardia. The heart beats are marked by atrial contractions or ventricular contractions. This results in multiple pairs of corresponding sets of atrial and ventricular intervals.

Repetitive rate calculator 544 calculates an average atrial rate based on each set of atrial intervals and a corresponding average ventricular rate based on the corresponding set of ventricular intervals. A pair of corresponding average atrial rate and average ventricular rate is calculated for each heart beat of the plurality of heart beats.

Tachycardia classification module 546 includes a persistence detector 579. Persistence detector 579 declares that the average ventricular rate is substantially higher than the average atrial rate when the average ventricular rate is persistently found to be substantially higher than the average atrial rate during the episode of the detected tachycardia. Tachycardia classification module 546 classifies the detected tachycardia as VT when persistence detector 579 declares that the average ventricular rate is substantially higher than the average atrial rate for the episode of the detected tachycardia.

Figure 6:
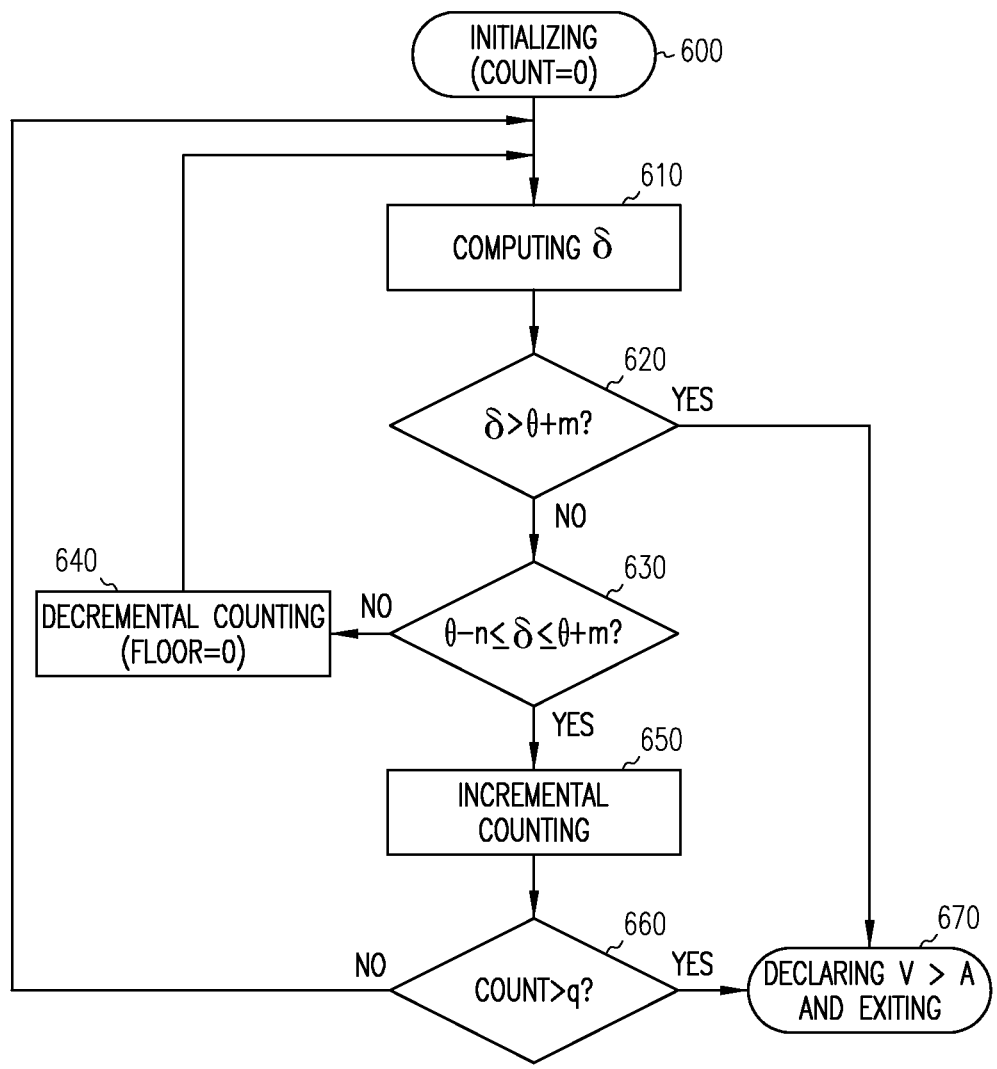
FIG. 6 is a flow chart illustrating an embodiment of a method for detecting the persistence of a ventricular tachycardia rhythm indication performed by the circuit of FIG. 5.

Persistence detector 579 detects a degree of persistence at which the average ventricular rate is substantially higher than the average atrial rate during the episode of the detected tachycardia. If the degree of persistence exceeds a predetermined persistence threshold, persistence detector 579 declares that the average ventricular rate is substantially higher than the average atrial rate for the episode. In one embodiment, persistence detector 579 executes a persistence detection algorithm that is illustrated by a flow chart in FIG. 6. As illustrated in FIG. 6, a persistence count ("COUNT") is initialized to zero at 600 for a persistence detection for an episode of detected tachycardia represented by a plurality of heart beats. For each heart beat, the difference between the average ventricular rate and the average atrial rate, δ, is computed at 610. If the difference δ is greater than a predetermined threshold difference θ by more than a margin m at 620, the average ventricular rate is declared to be substantially higher than the average atrial rate for the episode of the detected tachycardia at 670. Otherwise, the difference δ is compared to a difference window having a width n+m (referred to as an uncertainty zone), i.e. θ−n to θ+m, at 630. If the difference falls out of the difference window, i.e., δ<θ−n, at 630, the persistence count is decreased by one at 640. However, the count has a floor being zero. In other words, the persistence count is decreased at 640 only if the result is greater than zero. If the difference is within the difference window, i.e., θ−n≤δ≤↓+m, at 630, the persistence count is increased by one at 650. If the persistence count exceeds a predetermined persistence threshold q at 660, the average ventricular rate is declared to be substantially higher than the average atrial rate for the episode of the detected tachycardia at 670.

In one embodiment, as illustrated in FIG. 5, persistence detector 579 includes a repetitive rate comparator 576 and a VT counter 578. Repetitive rate comparator 576 compares each pair of corresponding average atrial rate and average ventricular rate at each heart beat for the plurality of heart beats representing the episode of the detected tachycardia. Whenever an average ventricular rate is substantially higher than the corresponding average ventricular rate, repetitive rate comparator 576 indicates a VT rhythm at its output. Otherwise, repetitive rate comparator 576 indicates a possible non-VT rhythm. The average ventricular rate is substantially higher than the corresponding average atrial rate when the difference between the two average rates reaches or exceeds a predetermined margin, such as about 10 beats per minute. VT counter 578 resets a persistence count to zero before the classification process for each detected tachycardia. In one embodiment, VT counter 578 increases the persistence count by one each time when a VT rhythm is indicated. Persistence detector 579 declares that the average ventricular rate is substantially higher than the average atrial rate for the episode of the detected tachycardia when the persistence count reaches a predetermined persistent threshold being the minimum number of persistence count required for classifying the detected tachycardia as VT. In another embodiment, VT counter 578 increases the persistence count by one each time when the VT rhythm is indicated and decreases the persistence count by one each time when the VT rhythm is not indicated (i.e., when a non-VT rhythm is indicated). The persistence count has a minimum value being zero. In a further embodiment, persistence detector 579 declares that the average ventricular rate is substantially higher than the average atrial rate for the episode of the detected tachycardia whenever an average ventricular rate is higher than the corresponding average atrial rate by a predetermined maximum margin. In other words, if at any time the average ventricular rate is higher than the corresponding average atrial rate by the predetermined maximum margin, the detected tachycardia is classified as VT regardless of the persistence count. In another further embodiment, persistence detector 579 includes a threshold adjustment circuit that dynamically adjusts the persistence threshold following each heart beat based on a difference between the average atrial rate and the corresponding average ventricular rate calculated for that heart beat.

Figure 7A:
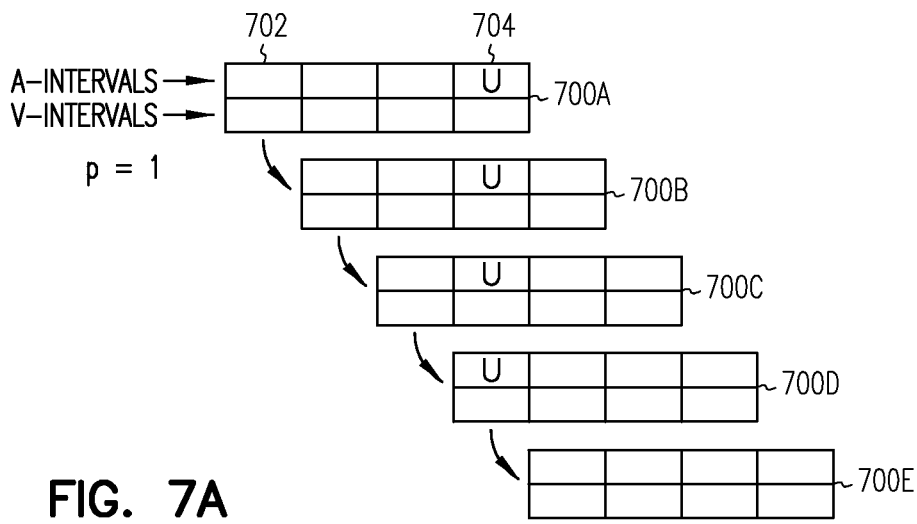
FIGS. 7A-D illustrate a method for reducing the effect of undersensed or oversensed beats in tachycardia classification performed by the circuit of FIG. 5.
Figure 7B:
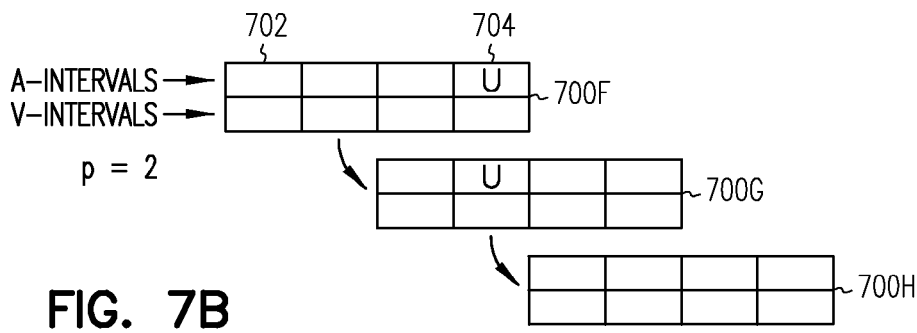
Figure 7C:
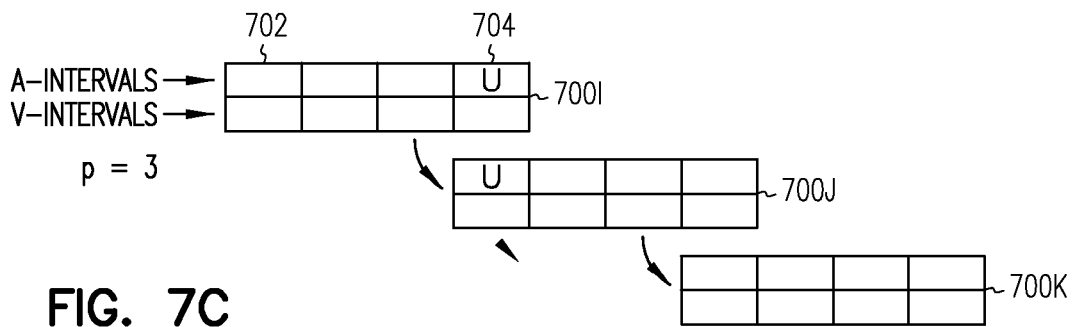
Figure 7D:
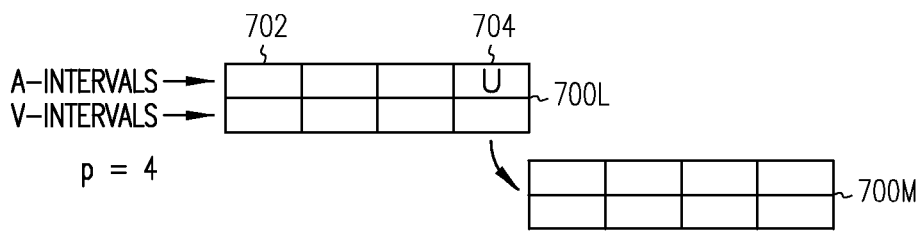

In one embodiment, rate accuracy enhancement module 542 includes a beat selector to select the plurality of heart beats representing the episode of the detected tachycardia. In one specific embodiment, the beat selector selects non-consecutive heart beats, such as every other heart beat or every third heart beat, to reduce the overall effect of beats that should be excluded from rate calculation, such as a PVC, an undersensed (missed) beat, or an oversensed beat (noise). FIGS. 7A-D illustrate such an approach to reducing the overall effect of such beats in the calculation of the average atrial and ventricular rates. In FIGS. 7A-D, p is the periodicity of repetitive interval selector 574. If p=1, the average atrial and ventricular rates are calculated on every consecutive heart beat. In other words, interval selector 574 moves the data set forward by one heart beat for each average rate calculation. If p=2, the average atrial and ventricular rates are calculated on every other heart beat. Generally, if p=N, the average atrial and ventricular rates are calculated on every $N^{th}$ heart beat. For illustrative purpose only, in FIGS. 7A-D, four consecutive atrial intervals are used to calculate the average atrial interval, and four corresponding consecutive ventricular intervals are used to calculate the corresponding average ventricular interval. Each atrial or ventricular interval is represented by a rectangle 702. Rectangles 704 (which are labeled by "U") each represent an atrial interval associated with an undersensed atrial event. Reference numbers 700A-M each represent a data set of the four atrial intervals for calculating the average atrial rate and the four ventricular intervals for calculating the average ventricular rates. As illustrated in FIG. 7A, when p=1, the average atrial and ventricular rates are calculated based on data sets 700A-E on every heart beat. The effect of atrial interval 704 is seen in four data sets, 700A-D, and is not seen in data set 700E. As illustrated in FIG. 7B, when p=2, the average atrial and ventricular rates are calculated based on data sets 700E-H on every second heart beat. The effect of atrial interval 704 is seen in two data sets, 700F and 700G, and is not seen in data set 700H. As illustrated in FIG. 7C, when p=3, the average atrial and ventricular rates are calculated based on data sets 700I-K on every third heart beat. The effect of atrial interval 704 is seen in two data sets, 700I and 700J, and is not seen in data set 700K. As illustrated in FIG. 7D, when p=4, the average atrial and ventricular rates are calculated based on data sets 700L and 700M on every fourth heart beat. The effect of atrial interval 704 is seen in one data set, 700L, and is not seen in data set 700M. Thus, as p increases, the persistence count is less affected by the undersensed or oversensed beats (or the associated intervals). In an alternative specific embodiment, the beat selector selects heart beats on a periodic basis, such as one heart beat every second or one heart beat every two seconds, to reduce the overall effect of beats that should be excluded from rate calculation, such as a PVC, an undersensed (missed) beat, or an oversensed beat (noise).

Figure 8:
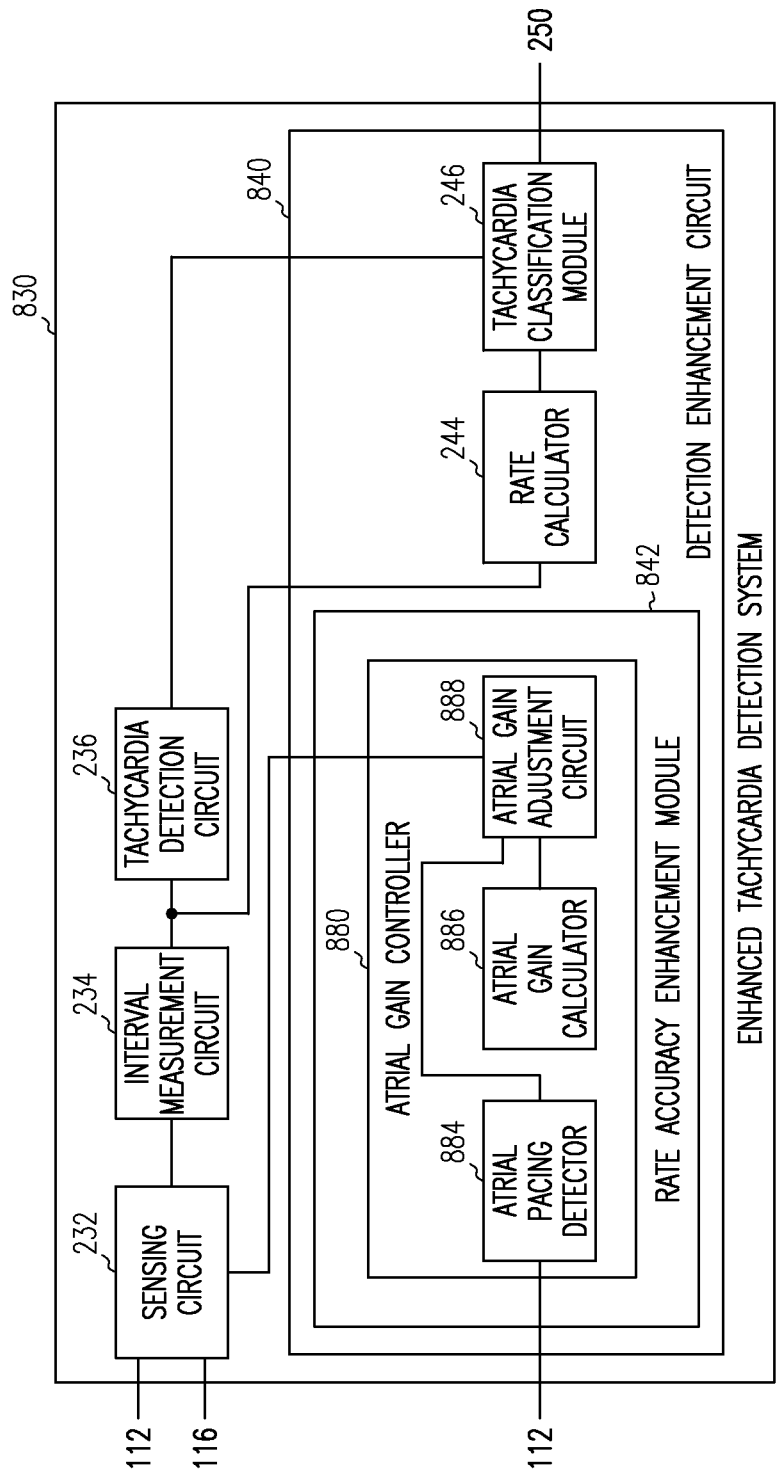
FIG. 8 is a block diagram illustrating an embodiment of the circuit of another enhanced tachycardia detection system.

FIG. 8 is a block diagram illustrating an embodiment of the circuit of another enhanced tachycardia detection system 830, which is another specific embodiment of enhanced tachycardia detection system 130. Enhanced tachycardia detection system 830 includes sensing circuit 232, interval measurement circuit 234, tachycardia detection circuit 236, and a detection enhancement circuit 840. Detection enhancement circuit 840 is another specific embodiment of detection enhancement circuit 240 and includes a rate accuracy enhancement module 842, rate calculator 244, and tachycardia classification module 246. Rate accuracy enhancement module 842 is another specific embodiment of rate accuracy enhancement module 242.

To enhance the accuracy of rate calculation performed by rate calculator 244, rate accuracy enhancement module 842 executes a rate accuracy enhancement algorithm designed to reduce the chance of atrial undersensing. Sensing circuit 232 has an adjustable atrial gain. Pulse delivery circuit 250 includes a pacing circuit to deliver at least atrial pacing pulses. Rate accuracy enhancement module 842 includes an atrial gain controller 880. Atrial gain controller 880 includes an atrial pacing detector 884, an atrial gain calculator 886, and an atrial gain adjustment circuit 888. Atrial pacing detector 880 detects atrial pacing pulses delivered from pulse delivery circuit 250. Atrial gain calculator 886 dynamically calculates a value for dynamically adjusting the atrial gain of sensing circuit 232. In one embodiment, an automatic gain adjustment algorithm provides for dynamical calculation of the atrial gain based on the amplitude of the atrial electrogram that changes over time. According to the automatic gain adjustment algorithm, the atrial gain is dynamically adjusted to the dynamically calculated value, except that after each delivery of an atrial pacing pulse, the atrial gain is set to a predetermined post-pacing value, known as the exception gain, regardless of the dynamically calculated value. When this predetermined post-pacing value is substantially smaller than the dynamically calculated value for the adjustable atrial gain, however, a risk of atrial undersensing may be created. Therefore, atrial gain adjustment circuit 888 compares the predetermined post-pacing value of the atrial gain to dynamically calculated value. After the delivery of each atrial pacing pulse, gain adjustment circuit 888 sets the atrial gain to the predetermined post-pacing value if the predetermined post-pacing value is greater than the dynamically calculated value, but to the dynamically calculated value if the predetermined post-pacing value is not greater than the dynamically calculated value. In various embodiments, atrial gain controller 880 can be included to dynamically adjust the atrial gain of sensing circuit 232 in any embodiment of the enhanced tachycardia detection system discussed in this document.

In an alternative embodiment, rate accuracy enhancement module 842 controls the threshold used in detecting atrial depolarizations (P waves) for the measurement of the atrial intervals. Rate accuracy enhancement module 842 includes an atrial threshold controller. The atrial threshold controller includes atrial pacing detector 884 and an atrial threshold adjustment circuit. After the delivery of each atrial pacing pulse, the threshold adjustment circuit 888 adjusts the threshold for detecting the atrial depolarizations to compensate for the possible undersensing effect of the exception gain. In another alternative embodiment, rate accuracy enhancement module 842 controls both the atrial gain and the threshold used in detecting atrial depolarizations and adjusts one or both of the gain and the threshold to avoid post-pacing undersensing of atrial depolarizations.

Figure 9:
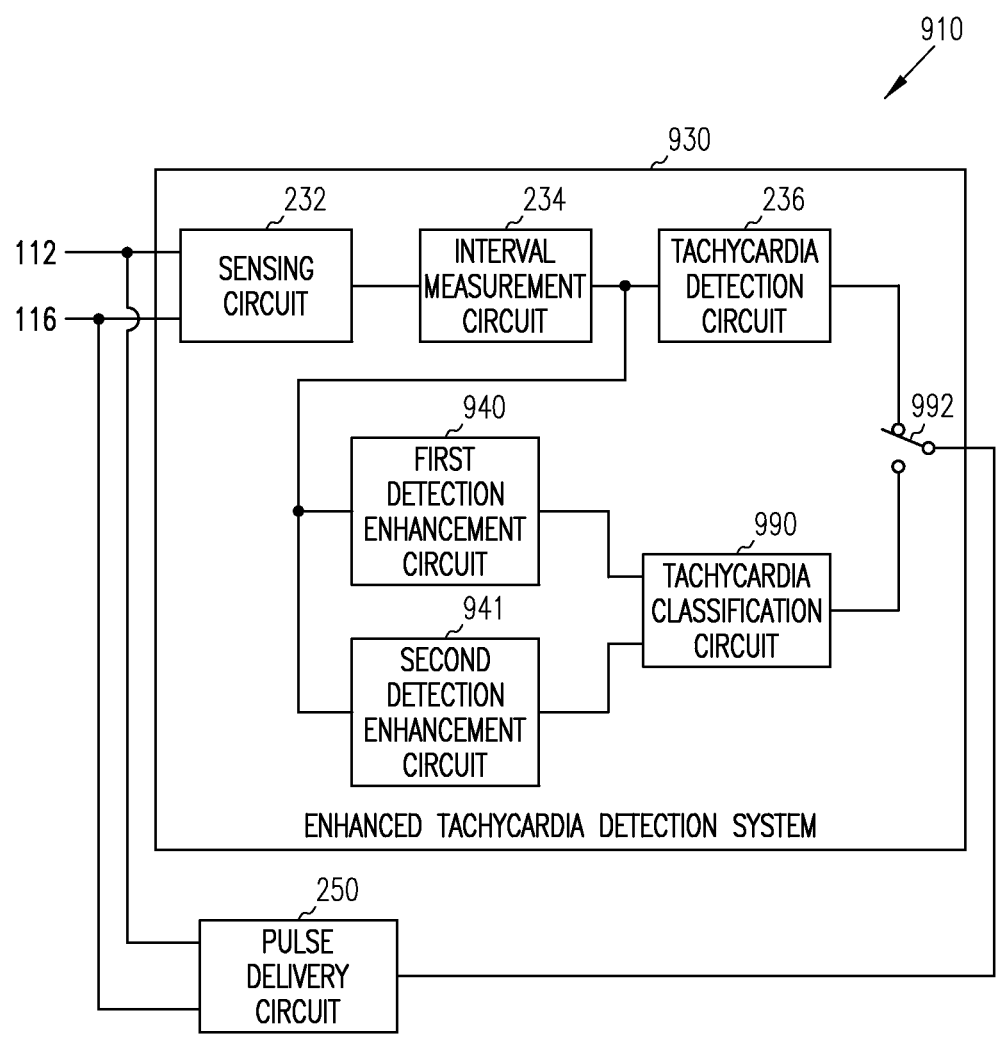
FIG. 9 is a block diagram illustrating another embodiment of portions of the circuit of the ICD.

FIG. 9 is a block diagram illustrating an embodiment of a circuit 910 including portions of the circuit of ICD 110. Circuit 910 is a further embodiment of circuit 210 and includes enhanced tachycardia detection system 930 and pulse delivery circuit 250.

Enhanced tachycardia detection system 930 includes sensing circuit 232, interval measurement circuit 234, tachycardia detection circuit 236, a first detection enhancement circuit 940, a second detection enhancement circuit 941, a tachycardia classification circuit 990, and a switch 992. After tachycardia detection circuit 236 detects a tachycardia, first detection enhancement circuit 940 classifies the detected tachycardia based on atrial and ventricular rates. Examples of first detection enhancement circuit 940 includes detection enhancement circuits 240, 340, 440, 540, and 840 as discussed above. Second detection enhancement circuit 941 classifies the detected tachycardia based on additional one or more processes such as detecting atrial fibrillation, assessing the ventricular onset rate of the detected tachycardia, and assessing the stability of the ventricular rate. Examples of such additional processes are discussed in U.S. Pat. No. 5,978,707, "APPARATUS AND METHOD FOR TREATING VENTRICULAR TACHYARRHYTHMIAS," assigned to Cardiac Pacemakers, Inc., which is incorporated by reference herein in its entirety. Tachycardia classification circuit 990 classifies the detected tachycardia based on the classifications produced by first detection enhancement circuit 940 and second detection enhancement circuit 941. In one embodiment, if first detection enhancement circuit 940 classifies the detected tachycardia as VT when the average ventricular rate is substantially higher than the average atrial rate, tachycardia classification circuit 990 classifies the detected tachycardia as VT regardless of any result of the classification processes performed by second detection enhancement circuit 941. Switch 992 is programmable for controlling the delivery of cardioversion/defibrillation pulses based on the rate-based detection of tachycardia with or without the detection enhancement. If the detection enhancement is not applied, pulse delivery circuit 250 delivers a cardioversion/defibrillation pulse when tachycardia detection circuit 236 detects a tachycardia. In one embodiment, tachycardia detection circuit 236 detects a tachycardia when a ventricular interval substantially falls below a threshold interval (i.e., a ventricular rate is substantially higher than a threshold rate). If the detection enhancement is applied, pulse delivery circuit 250 delivers a cardioversion/defibrillation pulse when tachycardia detection circuit 236 detects a tachycardia and tachycardia classification circuit 990 classifies the detected tachycardia as a VT.

Figure 10:
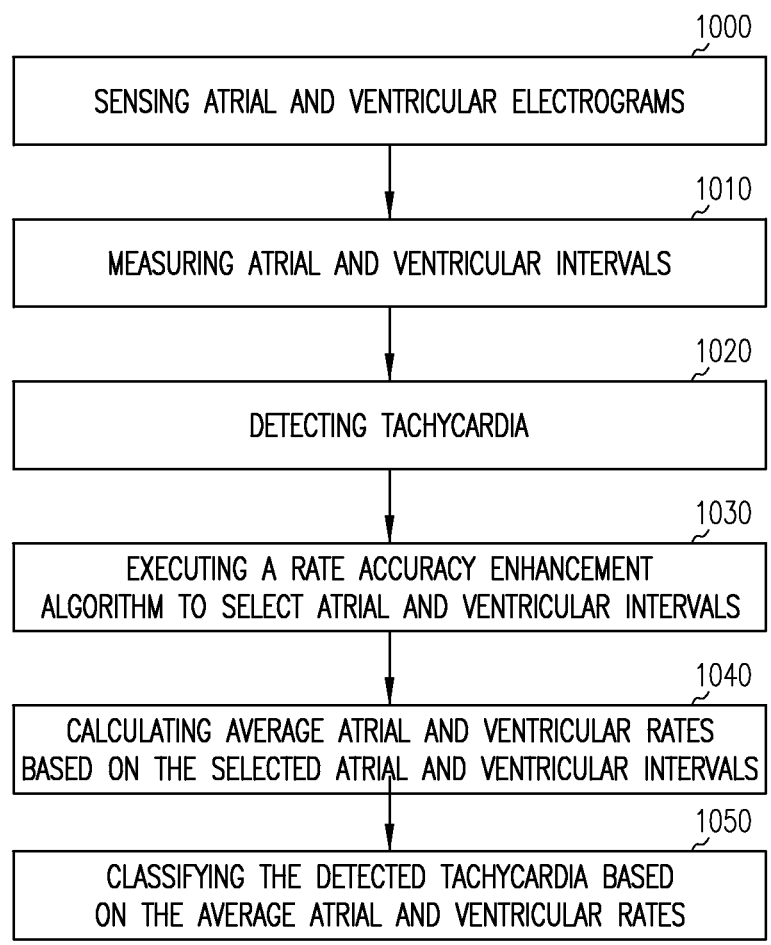
FIG. 10 is a flow chart illustrating an embodiment of a method for tachycardia detection enhancement.

FIG. 10 is a flow chart illustrating an embodiment of a method for tachycardia detection enhancement. The method includes sensitivity enhancement and specificity enhancement for VT detection based on heart rates, including atrial and ventricular rates.

An atrial electrogram and a ventricular electrogram are sensed at 1000. Atrial intervals are measured from the atrial electrogram, and ventricular intervals are measured from the ventricular electrogram, at 1010. Tachycardia is detected when one or more of the ventricular intervals fall below a tachycardia threshold interval, i.e., when the ventricular rate exceeds a tachycardia threshold rate, at 1020. A rate accuracy enhancement algorithm is executed to select at least one set of atrial intervals from the measured atrial intervals and one set of ventricular intervals from the measured ventricular intervals at 1030. An average atrial rate is calculated from the set of atrial intervals, and an average ventricular rate is calculated from the set of ventricular intervals, at 1040. A detected tachycardia is classified as VT at 1050 if the average ventricular rate is higher than the average atrial rate by a predetermined margin. The specificity of the VT detection increases with this predetermined margin. In one embodiment, the predetermined margin is about 10 beats per minute. In one embodiment, a ventricular cardioversion/defibrillation pulse is delivered after a detected tachycardia is classified as VT.

In one embodiment, the rate accuracy enhancement algorithm is executed to exclude outlier atrial/ventricular intervals, such as the longest and shortest atrial/ventricular intervals detected from a plurality of measured atrial/ventricular intervals, from the calculation of the average atrial/ventricular rates. A set of atrial intervals is selected from the measured atrial intervals, and a corresponding set of ventricular intervals is selected from the measured ventricular intervals. In one specific embodiment, the size of each of the sets of atrial/ventricular intervals is predetermined. In another specific embodiment, the size of each of the sets of atrial/ventricular intervals is determined based on one or more measured atrial intervals and/or one or more measured ventricular intervals. A subset of atrial intervals is selected from the set of atrial intervals, and a corresponding subset of ventricular intervals is selected from the corresponding set of ventricular intervals, by excluding the outlier atrial/ventricular intervals. The subset of atrial intervals is then used for the calculation of the average atrial rate, and the corresponding subset of ventricular intervals is then used for the calculation of the average ventricular rate. In one specific embodiment, the outlier atrial/ventricular intervals to be excluded include one or more shortest atrial intervals, one or more longest atrial intervals, one or more shortest ventricular intervals, and one or more longest ventricular intervals. In another specific embodiment, the outlier atrial/ventricular intervals to be excluded include one or more longest atrial intervals and one or more shortest ventricular intervals. In one specific embodiment, the number of the outlier atrial intervals to be excluded and the number of the outlier ventricular intervals to be excluded are determined based on one or more measured atrial intervals and/or one or more measured ventricular intervals.

In another embodiment, the rate accuracy enhancement algorithm is executed to determine the number of atrial and ventricular intervals used for calculating the average atrial and ventricular rates. The size of the set of atrial intervals and the size of the set of ventricular intervals are each determined based on one or more measured atrial intervals and/or one or more measured ventricular intervals. In one specific embodiment, the size of the set of atrial intervals and the size of the set of ventricular intervals are equal.

In another embodiment, the rate accuracy enhancement algorithm is executed to enhance the accuracy of VT detection and classification by repeating the rate comparison. This reduces the effect of intervals associated with undersensed or oversensed beats in the VT classification process. A set of atrial intervals is selected from the measured atrial intervals, and a corresponding set of ventricular intervals from the measured ventricular intervals, for each heart beat of a plurality of heart beats. The heart beats are marked by atrial or ventricular contractions. This results in multiple pairs of corresponding sets of atrial and ventricular intervals. In one specific embodiment, the plurality of heart beats includes consecutive heart beats. In another specific embodiment, the plurality of heart beats includes nonconsecutive heart beats, such as every other heart beats, every third heart beats, or so forth. An average atrial rate and an average ventricular rate are calculated from each pair of corresponding sets of atrial and ventricular intervals. The detected tachycardia is classified as VT if the average ventricular rate is higher than the average atrial rate by a predetermined margin for at least a predetermined number of heart beats. If the average ventricular rate is substantially higher than the corresponding average atrial rate for a heart beat, a VT beat is indicated for that heart beat. Otherwise, a non-VT beat is indicated for that heart beat. In one specific embodiment, a count for VT beats is increased by one each time when a VT beat is declared. In another specific embodiment, a count for VT beats is increased by one each time when a VT beat is declared and decreased by one when a non-VT beat is declared. The detected tachycardia is classified as VT when the count reaches a predetermined persistence threshold count. In one specific number, the detected tachycardia is also classified as VT if, for any heart beat, the average ventricular rate is higher than the corresponding average atrial rate by a predetermined maximum margin. In one specific embodiment, the persistence threshold is dynamically adjusted based on the difference between the average atrial rate and the corresponding average ventricular rate for one or more heart rates.

In another embodiment, the rate accuracy enhancement algorithm is executed to reduce the possibility of atrial undersensing. In this embodiment, pacing pulses are delivered to an atrium on demand. According to an automatic gain adjustment algorithm, the gain for sensing the atrial electrogram is dynamically adjusted based on at least the amplitude of the sensed atrial electrogram. After each delivery of an atrial pacing pulse, the atrial gain is set to a predetermined post-pacing value, regardless of the dynamically calculated value. The rate accuracy enhancement algorithm modifies the automatic gain adjustment algorithm. According to the rate accuracy enhancement algorithm, the value of the atrial gain is still dynamically calculated based on the amplitude of the atrial electrogram. The dynamically calculated value is compared to the predetermined post-pacing value. After a delivery of an atrial pacing pulse, the atrial gain is set to the predetermined post-pacing value if the predetermined value is greater than the dynamically calculated value and to the dynamically calculated value if the predetermined value is not greater than the dynamically calculated value.

It is to be understood that detection and classification of VT can be performed using variations of the embodiments, including various combinations of the embodiments, discussed above without deviating from the concepts embedded in these embodiments. For example, two or more of the specific embodiments of enhanced tachycardia detection system 130, illustrated as systems 330, 430, 530, and 630, can be combined for further enhancement of VT detection.

It is to be understood that wherever a cardiac interval (such as the atrial interval or the ventricular interval) is used for the tachycardia detection and/or classification as discussed above, its corresponding cardiac rate (i.e., the atrial rate and the ventricular rate) can instead be used, and vice versa, depending on specific design considerations. The relationship between a rate and an interval, as used in this document, is the relationship between a frequency and its corresponding period. If a rate is given in beats per minute (bpm), its corresponding interval in millisecond is calculated by dividing 60,000 by the rate (where 60,000 is the number of milliseconds in a minute). Any process, such as tachycardia detection, using an interval can be modified accordingly to use the corresponding rate instead. For example, if a tachycardia is detected when the ventricular interval falls below a tachycardia threshold interval, an equivalent process is to detect the tachycardia when the ventricular rate is higher than a corresponding tachycardia threshold rate. The appended claims should be construed to cover such variations. For example, an atrial interval should be construed as equivalent to the corresponding atrial rate, and a ventricular interval should be construed as equivalent to the corresponding ventricular rate, respectively.

While the rate accuracy enhancement is discussed above using its application in a tachycardia detection system as a specific example, a circuit for enhancing the accuracy in calculating average atrial and/or ventricular rates based on measured cardiac intervals, as illustrated by rate accuracy enhancement modules 242, 342, 442, 542, and 842, is applicable in any average rate calculations. Such rate calculation is triggered by any event that is predetermined to initiate a process during which one or more average heart rates, including atrial and/or ventricular rates, are calculated. Examples of such a triggering event include a cardiac event such as a depolarization in the atria, the ventricles, and the atrioventricular node and bundle, a detection of an arrhythmic episode, a predetermined feature in a non-cardiac signal such as a respiratory signal or a blood pressure or flow signal, a heart sound, and a physical activity level.

It is to be understood that the above detailed description is intended to be illustrative, and not restrictive. For example, enhanced tachycardia detection system 130, including its various embodiments discussed above, is not limited to applications in an ICD, but may be incorporated into any arrhythmia analysis system, such as a computer program for analyzing pre-collected cardiac data. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for classifying a detected tachycardia using measured atrial intervals and measured ventricular intervals, the system comprising:
    a detection enhancement circuit including:
        a first selection circuit including a set size circuit configured to determine a size of a set of atrial intervals and a size of a set of ventricular intervals based on a measured atrial or ventricular rate, the first selection circuit configured to select the set of atrial intervals from the measured atrial intervals according to the determined size of the set of atrial intervals and the set of ventricular intervals from the measured ventricular intervals according to the determined size of the set of ventricular intervals;
        a second selection circuit configured to select a subset of atrial intervals from the set of atrial intervals and a subset of ventricular intervals from the set of ventricular intervals, the second selection circuit including an interval exclusion circuit configured to exclude one or more intervals from the set of atrial intervals and the set of ventricular intervals based on predetermined exclusion criteria;
    a rate calculator configured to calculate an average atrial rate using the subset of atrial intervals and an average ventricular rate using the subset of ventricular intervals; and
    a tachycardia classification circuit configured to classify the detected tachycardia using the average atrial rate and the average ventricular rate.

2. The system of claim 1, wherein the tachycardia classification circuit is configured to classify the detected tachycardia as ventricular tachycardia (VT) when the average ventricular rate is substantially higher than the average atrial rate.

3. The system of claim 1, wherein the interval exclusion circuit is configured to exclude a predetermined number of intervals from each of the set of atrial intervals and the set of ventricular intervals.

4. The system of claim 1, wherein the interval exclusion circuit is configured to determine a number of intervals to be excluded from each of the set of atrial intervals and the set of ventricular intervals based on at least one of the measured atrial intervals and the measured ventricular intervals.

5. The system of claim 1, wherein the interval exclusion circuit is configured to exclude one or more shortest intervals and one or more longest intervals from the set of atrial intervals and the set of ventricular intervals.

6. The system of claim 5, wherein the interval exclusion circuit is configured to exclude one or more shortest atrial intervals and one or more longest atrial intervals from the set of atrial intervals and exclude one or more shortest ventricular intervals and one or more longest ventricular intervals from the set of ventricular intervals.

7. The system of claim 5, wherein the interval exclusion circuit is configured to exclude one or more longest atrial intervals from the set of atrial intervals and exclude one or more shortest ventricular intervals from the set of ventricular intervals.

8. The system of claim 1, wherein the set size circuit is configured to determine the size of the set of atrial intervals and the size of the set of ventricular intervals based on one or more intervals of the measured atrial intervals.

9. The system of claim 1, wherein the set size circuit is configured to determine the size of the set of atrial intervals and the size of the set of ventricular intervals based on one or more intervals of the measured ventricular intervals.

10. The system of claim 9, wherein the set size circuit is configured to determine the size of the set of atrial intervals and the size of the set of ventricular intervals based on one or more intervals of the measured atrial intervals and the one or more intervals of the measured ventricular intervals.

11. A method for operating an implantable cardioverter/defibrillator (ICD) to classify a detected tachycardia using measured atrial intervals and measured ventricular intervals, the method comprising:
    determining a size of a set of atrial intervals and a size of a set of ventricular intervals based on a measured atrial or ventricular rate;
    selecting the set of atrial intervals from the measured atrial intervals according to the determined size of the set of atrial intervals and the set of ventricular intervals from the measured ventricular intervals according to the determined size of the set of ventricular intervals using the ICD;
    selecting a subset of atrial intervals from the set of atrial intervals and a subset of ventricular intervals from the set of ventricular intervals by excluding one or more intervals from each of the set of atrial intervals and the set of ventricular intervals according to predetermined exclusion criteria using the ICD;
    calculating an average atrial rate using the subset of atrial intervals and an average ventricular rate using the subset of ventricular intervals using the ICD; and
    classifying the detected tachycardia using the average atrial rate and the average ventricular rate using the ICD.

12. The method of claim 11, wherein classifying the detected tachycardia comprises classifying the detected tachycardia as ventricular tachycardia (VT) when the average ventricular rate is substantially higher than the average atrial rate.

13. The method of claim 11, wherein selecting the subset of atrial intervals and the subset of ventricular intervals comprises excluding one or more shortest intervals and one or more longest intervals from the set of atrial intervals and the set of ventricular intervals.

14. The method of claim 13, wherein excluding the one or more intervals from each of the set of atrial intervals and the set of ventricular intervals comprises excluding a predetermined number of intervals from each of the set of atrial intervals and the set of ventricular intervals.

15. The method of claim 13, comprising determining a number of atrial intervals to be excluded from the set of atrial intervals and a number of ventricular intervals to be excluded from the set of ventricular intervals based on at least one of the measured atrial intervals and the measured ventricular intervals.

16. The method of claim 13, wherein selecting the subset of atrial intervals and the subset of ventricular intervals comprises excluding one or more shortest atrial intervals and one or more longest atrial intervals from the set of atrial intervals and excluding one or more shortest ventricular intervals and one or more longest ventricular intervals from the set of ventricular intervals.

17. The method of claim 13, wherein selecting the subset of atrial intervals and the subset of ventricular intervals comprises excluding one or more longest atrial intervals from the set of atrial intervals and excluding one or more shortest ventricular intervals from the set of ventricular intervals.

18. The method of claim 11, wherein determining the size of the set of atrial intervals and the size of the set of ventricular intervals comprises determining the size of the set of atrial intervals and the size of the set of ventricular intervals based on one or more intervals of the measured atrial intervals.

19. The method of claim 11, wherein determining the size of the set of atrial intervals and the size of the set of ventricular intervals comprises determining the size of the set of atrial intervals and the size of the set of ventricular intervals based on one or more intervals of the measured ventricular intervals.

20. The method of claim 19, wherein determining the size of the set of atrial intervals and the size of the set of ventricular intervals comprises determining the size of the set of atrial intervals and the size of the set of ventricular intervals based on one or more intervals of the measured atrial intervals and the one or more intervals of the measured ventricular intervals.

\* \* \* \* \*